United States Patent [19]

Goldmann et al.

[11] Patent Number: 4,772,612

[45] Date of Patent: Sep. 20, 1988

[54] CIRCULATION-ACTIVE 1,4-DIHYDROPYRIDINES

[75] Inventors: Siegfried Goldmann, Wuppertal; Jürgen Stoltefuss, Haan; Gerhard Franckowiak; Rainer Gross, both of Wuppertal; Matthias Schramm, Cologne, all of Fed. Rep. of Germany; Günter Thomas, Garbagnate, Italy

[73] Assignee: Bayer Aktiengesellschaft, Leverkusen, Fed. Rep. of Germany

[21] Appl. No.: 870,042

[22] Filed: Jun. 3, 1986

[30] Foreign Application Priority Data

Jun. 19, 1985 [DE] Fed. Rep. of Germany ....... 3521761

[51] Int. Cl.⁴ .................. A61K 31/455; C07D 211/90; C07D 491/048; C07D 401/12

[52] U.S. Cl. ..................... 514/302; 514/332; 514/335; 514/336; 514/352; 546/116; 546/261; 546/263; 546/265; 546/283; 546/284; 546/286; 546/312; 546/321

[58] Field of Search ............... 546/321, 312, 116, 286, 546/261, 263, 265, 283, 284; 514/356, 302, 352, 332, 335, 336

[56] References Cited

FOREIGN PATENT DOCUMENTS 0088274 9/1983 European Pat. Off. .

OTHER PUBLICATIONS

Chemical Abstracts, vol. 103, 1985, p. 700, 103:160398j.

Chemical Abstracts, vol. 98, 1983, p. 536, 98:89135s.

Primary Examiner—M. C. Lee
Assistant Examiner—Dale A. Bjorkman
Attorney, Agent, or Firm—Sprung Horn Kramer & Woods

[57] ABSTRACT

Novel circulation active dihydropyridines of the formula

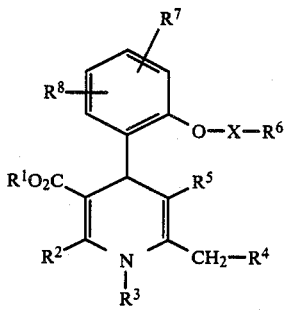

in which

X is CO, $SO_2$ or CONH, $R^4$ is H, OH, alkyl, halogen, acyloxy, alkoxyalkoxy, aralkyloxy, or together with $R^5$ forms a heterocyclic ring, and the other radicals are conventional in the dihydropyridine art, and pharmaceutically acceptable salts thereof.

9 Claims, No Drawings

CIRCULATION-ACTIVE 1,4-DIHYDROPYRIDINES

The present invention relates to new 1,4-dihydropyridines, to processes for their preparation and to their use in medicaments, in particular in agents having an effect on the circulation.

It has already been disclosed that 1,4-dihydropyridines have vasodilator properties and can be used as coronary agents and antihypertensives (compare British Pat Nos. 1,173,062 and 1,358,951; German Offenlegungsschriften Nos. 2,629,892 and 2,752,820). It has furthermore been disclosed that 1,4-dihydropyridines bring about inhibition of the contractility of smooth and cardiac muscles and can be used for the treatment of coronary and vascular diseases (compare Fleckenstein, Ann. Rev. Pharmacol. Toxicol. 17, 149–166 (1977)).

It could not have been foreseen, knowing these properties of the dihydropyridines, that the compounds, according to the invention, of this class of substances have a contractility-enhancing and, on the myocardium, positive inotropic action.

The invention relates to new 1,4-dihydropyridines of the general formula (I)

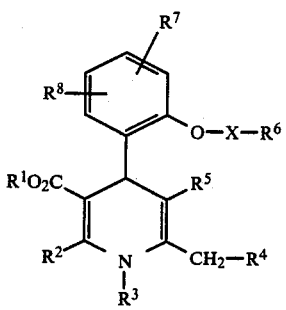

in which $R^1$ represents straight-chain, branched or cyclic alkyl or alkenyl each of which has up to 12 C atoms and which is optionally interrupted in the chain by several oxygen and/or sulphur atoms and is optionally substituted by phenyl, cyano, hydroxyl, one or more halogen, nitro, carboxyl, $C_1$–$C_6$-alkoxycarbonyl, $C_1$–$C_6$-alkylsulphonyl, sulphamoyl or by an amino group, it being possible for the amino group to carry one or two identical or different substituents from the group comprising $C_1$–$C_6$-alkyl, $C_6$–$C_{10}$-aryl, $C_7$–$C_{14}$-aralkyl or $C_2$–$C_7$-acyl, $R^2$ represents straight-chain or branched alkyl having up to 6 C atoms, which is optionally substituted by one or more halogen, hydroxyl or phenyl, or represents cyano, $R^3$ represents hydrogen, or represents straight-chain or branched alkyl having up to 6 C atoms, $R^4$ represents hydrogen or hydroxyl, represents straight-chain or branched alkyl having up to 6 C atoms, represents halogen, or represents a group O—Y, wherein Y represents an alcohol-protective group such as $C_2$–$C_7$-acyl, $C_1$–$C_4$-alkoxymethyl or $C_7$–$C_{14}$-aralkyl, $R^5$ represents hydrogen, represents nitro, represents cyano or represents a group $COR^9$, $CO_2R^9$ or $SO_2R^9$, wherein $R^9$ and $R^4$ together denote a bond, X represents $>C=O$, $-SO_2-$ or $-CO-NH-$, $R^6$ represents straight-chain, branched or cyclic alkyl or alkenyl each of which has up to 20 C atoms and is optionally substituted by aryl (6, 10 C atoms), one or more halogen, nitro, carboxyl, $C_1$–$C_6$-alkoxycarbonyl, hydroxyl or cyano, represents 5- to 7-membered, saturated or unsaturated heterocyclyl having 1 to 2 nitrogen, oxygen and/or sulphur as hetero-atoms and optionally being substituted by halogen or $C_1$–$C_6$-alkyl, represents aryl having up to 16 C atoms which is optionally substituted by up to five identical or different substituents from the series comprising halogen, nitro, $C_1$–$C_8$alkyl, $C_1$–$C_5$-alkoxy, $C_1$–$C_5$-alkylthio, $C_1$–$C_3$-halogenoalkyl, $C_1$–$C_3$-halogenoalkoxy, $C_1$–$C_3$-halogenoalkylthio, cyano, $SO_2NH_2$, $C_1$–$C_6$-alkylsulphonyl, $C_1$–$C_6$-alkoxycarbonyl or amino, it being possible or this amino group to carry one or two substituents from the series comprising $C_1$–$C_4$-alkyl, phenyl or $C_2$–$C_7$-acyl, or represents the radical

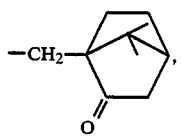

and $R^7$ and $R^8$ are identical or different and represent hydrogen, represent $C_1$–$C_8$-alkoxy, represent halogen, represent $C_1$–$C_8$-alkyl, represent nitro, represent cyano, or represent trifluoromethyl, and to their salts.

Preferred compounds of the general formula I are those in which $R^1$ represents straight-chain, branched or cyclic alkyl or alkenyl each of which has up to 10 C atoms and is optionally interrupted by up to 3 oxygen and/or sulphur atoms in the chain and is optionally substituted by phenyl, cyano, hydroxyl, one or more fluorine, chlorine, bromine, carboxyl, $C_1$–$C_4$-alkoxycarbonyl, $C_1$–$C_4$-alkylsulphonyl or by an amino group, it being possible for the amino group to carry one or two identical or different substituents from the group comprising $C_1$–$C_4$-alkyl, phenyl, benzyl, acetyl or benzoyl, $R^2$ represents straight-chain or branched alkyl having up to 4 C atoms, which is optionally substituted by one or more fluorine, chlorine, bromine, phenyl or hydroxyl, or represents cyano, $R^3$ represents hydrogen, or represents straight-chain or branched alkyl having up to 4 C atoms, $R^4$ represents hydrogen, or hydroxyl, represents straight-chain or branched alkyl having up to 4 C atoms, represents fluorine, chlorine or bromine, or represents a group O—Y, wherein Y represents acetyl, methoxymethyl or benzyl, $R^5$ represents nitro, represents cyano, or represents the group $CO_2R^9$, wherein $R^9$ and $R^4$ together denote a direct bond, X represents $>C=O$, $-SO_2-$ or $-CO-NH-$, $R^6$ represents straight-chain, branched or cyclic alkyl or alkenyl each of which has up to 18 C atoms and is optionally substituted by phenyl, one or more fluorine, chlorine, nitro, carboxyl or $C_1$-$C_4$-alkoxycarbonyl, or represents thienyl, furyl, pyrrolyl, pyridyl, pyrimidyl, pyrazinyl or pyridazinyl each of which is optionally substituted by flourine, chlorine, bromine or $C_1$-$C_4$-alkyl, or represents $C_6$-$C_{10}$-aryl which is optionally substituted by up to 4 identical or different substituents from the series comprising fluorine, chlorine, bromine, nitro, $C_1$-$C_6$-alkyl, $C_1$-$C_3$-alkoxy, $C_1$-$C_3$-alkylthio, $C_1$-$C_4$-alkoxycarbonyl, $C_1$-$C_4$-alkylsulphonyl, trifluoromethoxy, trifluoromethylthio, trifluoromethyl or amino, it being possible for this amino group to carry one or two substituents from the series comprising benzoyl, acetyl, phenyl or methyl, or represents the radical

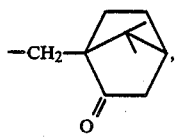

and $R^7$ and $R^8$ are identical or different and represent hydrogen, represent $C_1$-$C_6$-alkoxy, represent fluorine, chlorine or bromine, represent $C_1$-$C_6$-alkyl, represent nitro, represent cyano or represent trifluoromethyl, and their salts.

Preferred compounds of the general formula I are those in which $R^1$ represents straight-chain, branched or cyclic alkyl or alkenyl each of which has up to 8 C atoms and is optionally interrupted in the chain by one oxygen or sulphur atom and is optionally substituted by phenyl, cyano, one or more fluorine or N-benzyl-N-methylamino, $R^2$ represents methyl, hydroxymethyl or ethyl, or represents cyano, $R^3$ represents hydrogen, or represents methyl or ethyl, $R^4$ represents hydrogen or hydroxyl, represents methyl or ethyl, represents chlorine or bromine, or represents a group O—Y, wherein Y represents acetyl, $R^5$ represents nitro, or represents $CO_2R^9$, wherein $R^9$ and $R^4$ together denote a direct bond, X represent $>C=O$, $-SO_2-$ or $-CO-NH-$, $R^6$ represents straight-chain, branched or cyclic alkyl or alkenyl each of which has up to 16 C atoms and is optionally substituted by phenyl or one or more fluorine or chlorine, represents thienyl, furyl or pyridyl which is optionally substituted by chlorine or methyl, or represents phenyl or naphthyl each of which optionally carries up to 3 identical or different substituents from the series comprising fluorine, chlorine, nitro, $C_1$-$C_4$-alkyl, methoxy, methylthio, trifluoromethoxy, trifluoromethylthio, trifluoromethyl or acetylamino, or represents the radical

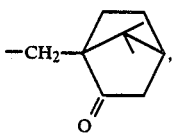

and $R^7$ and $R^8$ are identical or different and represent hydrogen, represent $C_1$-$C_4$-alkoxy, represent chlorine, represent $C_1$-$C_4$-alkyl, represent nitro, or represent trifluoromethyl, and their salts.

The substances according to the invention can be n the form of their salts. In general, these are salts of the substances according to the invention with inorganic or organic acids. However, the physiologically acceptable salts of the substances according to the invention with inorganic and organic acids are preferred. Examples which may be mentioned are hydrogen halides, hydrogen sulphates, sulphates, hydrogen phosphates, acetates, maleates, citrates, fumarates, tartrates, lactates or benzoates.

The compounds of the formula I, according to the invention, in which $R^1$-$R^8$ and X have the abovementioned meaning, but $R^5$ may not represent the radical $CO_2R^9$, are obtained when

[A] aldehydes of the general formula (II)

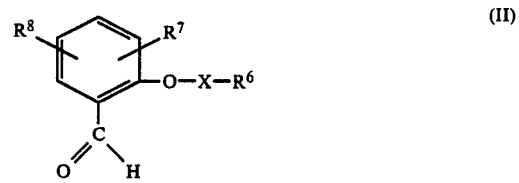

in which $R^6$, $R^7$, $R^8$ and X have the abovementioned meaning, and keto compounds of the general formula (III)

in which $R^1$ and $R^2$ have the abovementioned meaning, are reacted with keto compound of the general formula (IV)

in which $R^4$ and $R^5$ have the abovementioned mean:ng, and amines of the general formula (V)

in which $R^3$ has the abovementioned meaning, where appropriate in the presence of water and/or inert organic solvents, or when

[B] aldehydes of the general formula (II) are reacted with keto compounds of the general formula (III) and enamines of the general formula (VI)

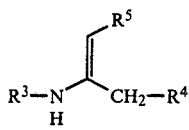

in which
R³, R⁴ and R⁵ have the abovementioned meaning,
where appropriate in the presence of water and/or inert organic solvents,
or when

[C] aldehydes of the general formula (II) are reacted with keto compounds of the general formula (IV) and enamines of the general formula (VII)

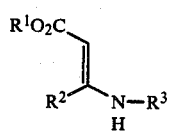

in which
R¹, R² and R³ have the abovementioned meaning,
where appropriate in the presence of water and/or inert organic solvents,
or when

[D] keto compounds of the general formula (III) are reacted with amines of the general formula (V) and ylidene compounds of the general formula (VIII)

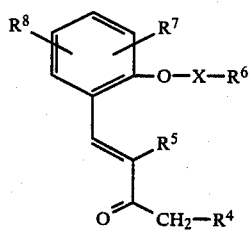

in which
R⁴, R⁵, R⁶, R⁷, R⁸ and X have the abovementioned meaning,
where appropriate in the presence of water and/or inert organic solvents,
or when

[E] keto compounds of the general formula (IV) are reacted with amines of the general formula (V) and ylidene compounds of the general formula (IX)

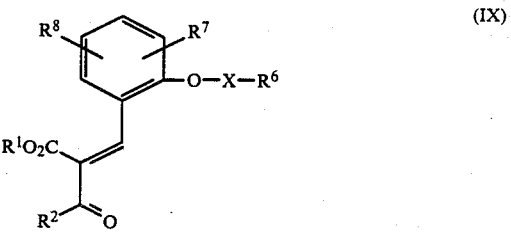

in which
R¹, R², R⁶, R⁷, R⁸ and X have the abovementioned meaning,
where appropriate in the presence of water and/or inert organic solvents,
or when

[F] ylidene compounds of the general formula (VIII) are reacted with enamines of the general formula (VII), where appropriate in the presence of water and/or inert organic solvents,
or when

[G] ylidene compounds of the general formula (IX) are reacted with enamines of the general formula (VI), where appropriate in the presence of water and/or inert organic solvents.

Depending on the nature of the starting materials used, the synthesis of the compounds (I) by processes A to G can be illustrated by the following scheme:

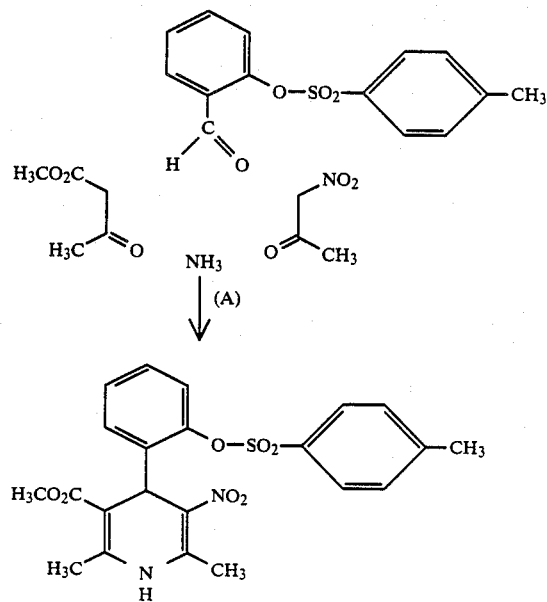

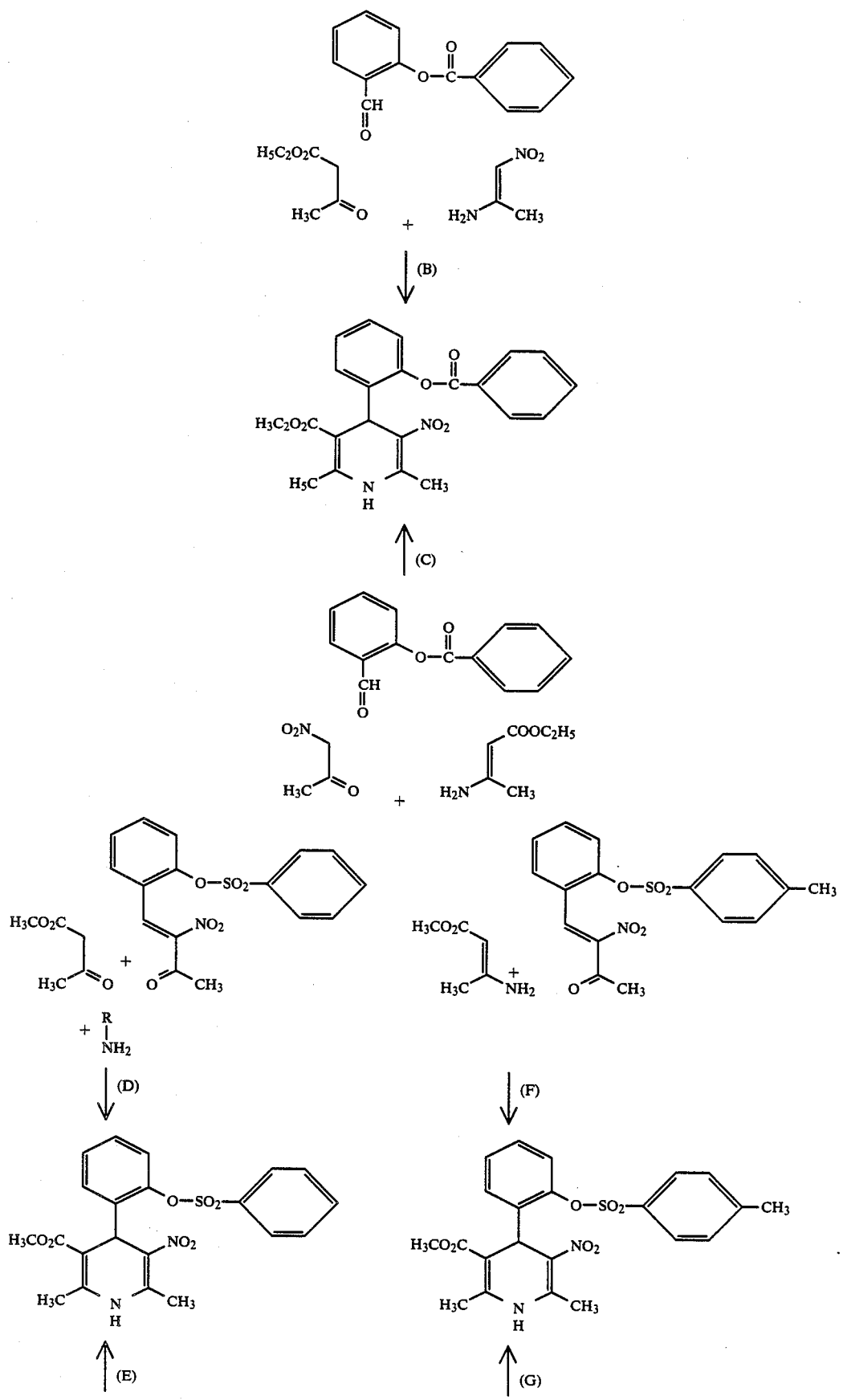

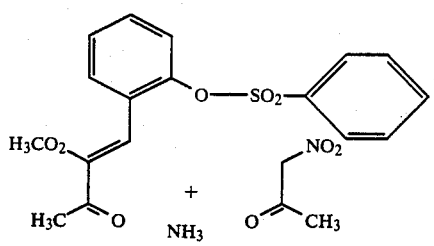 + 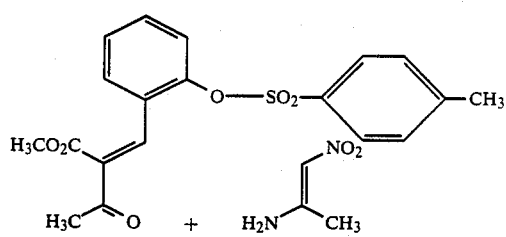

The aldehydes of the general formula II which are used as starting materials are known or can be prepared by methods known from the literature (compare W. J. Dale, H. E. Hennis J. Am. Chem. Soc. 78, 2543 (1956)).

The keto compounds III and IV used as starting materials are known or can be prepared by methods known from the literature (compare D. Borrmann in Houben-Weyl "Methoden der organischen Chemie" (Methods of Organic Chemistry) VII/4, 230 et seq. (1968); P. Pollet, S. Gelin, Tetrahedron 34, 1453 (1978); Y. Oikawa, K. Sugano, O. Yonemitsu, J. Org. Chem. 43, 2087 (1978); C. W. Scaife, J. Chem. Soc. (London) 1946, 1100; C. D. Hurd, M. E. Nilson, J. Org. Chem. 20, 927 (1955)).

Compounds of the formula V are known and can be obtained commercially.

The enamines VI and VII used as starting materials are known or can be prepared by methods known from the literature (compare S. A. Glickman, A. C. Cope, J. Am. Chem. Soc. 67, 1017 (1945); H. Böhme, K.-H. Weisel, Arch. Pharm. 310, 30 (1977)).

The ylidene compounds VIII and IX used as starting materials are known or can be prepared by methods known from the literature (compare G. Jones "The Knoevenagel Condensation", Organic Reactions XV, 204 et seq. (1967); for $R^5=NO_2$, compare W. Sassenberg, A. Dornow, Liebigs Ann. Chem. 602, 14 (1957)).

Suitable diluents for the processes A to G are all inert organic solvents. These include, preferably, alcohols such as methanol, ethanol, n- and iso-propanol, ethers such as diethyl ether, tetrahydrofuran, dioxane or glycol monoethyl or diethyl ether, glacial acetic acid, pyridine, dimethylformamide, dimethyl sulphoxide, acetonitrile or hexamethylphosphoric triamide.

The reaction temperatures for processes A to G can be varied within wide limits. In general they are in the range from 10° C. to 200° C., preferably from 20° C. to 15° C.

The reaction can be carried out under atmospheric pressure as well as under elevated pressure. In general, it is carried out under atmospheric pressure.

When carrying out the processes according to the invention, the ratio of the substances involved in the reaction is arbitrary. However, in general molar amounts of the reactants are used.

Processes B, C, F and G are the preferred processes for the preparation of the compounds I in which $R^1$ to $R^8$ and X have the indicated meaning, but $R^5$ may not represent the group $CO_2R^9$. Processes B and C are particularly preferred.

The compounds of the general formula I, according to the invention, in which $R^1$-$R^3$, $R^6$-$R^8$ and X have the indicated meaning, $R^5$ represents the group $CO_2R^9$, and $R^4$ and $R^9$ together represent a bond, are obtained when [H] aldehydes of the general formula II

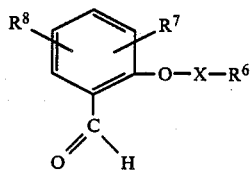

in which $R^6$-$R^8$ and X have the abovementioned meaning, are reacted with keto compounds of the general formula III

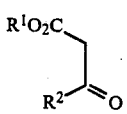

in which $R^1$ and $R^2$ have the abovementioned meaning, and with enamines of the formula X

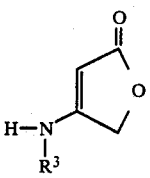

in which $R^3$ has the abovementioned meaning, where appropriate in the presence of water and/or inert organic solvents, or when

[I] dihydropyridines of the general formula XI

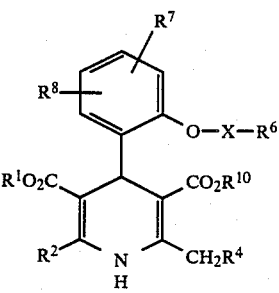

in which $R^1$-$R^3$, $R^6$-$R^8$ and X have the abovementioned meaning, $R^4$ represents halogen, represents a group O—Y, wherein Y has the abovementioned meaning, and $R^{10}$ represents straight-chain or branched alkyl having up to 6 C atoms,
are cyclized, where appropriate in the presence of inert organic solvents and, where appropriate, in the presence of bases, or when $R^4$ represents halogen, are pyrolyzed with or without solvents.

Depending on the nature of the starting materials used, the synthesis of the substances I by process H or I can be illustrated by the following schemes:

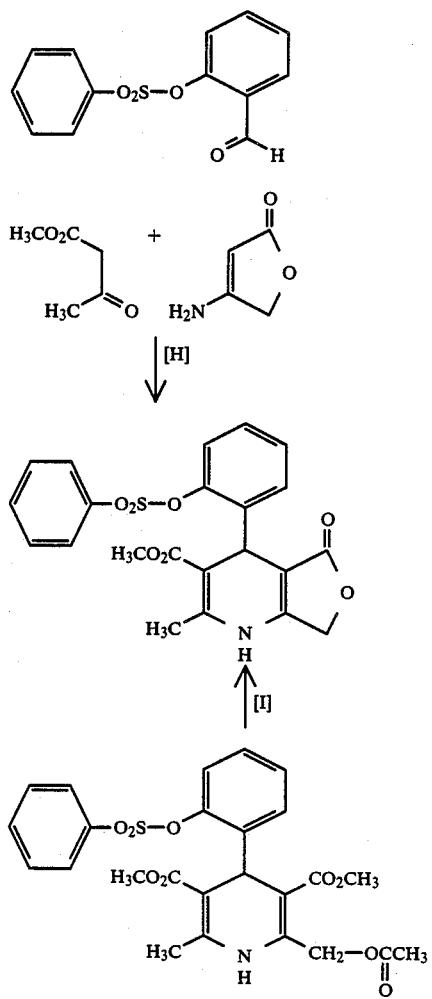

The compounds II, III and X used as starting materials are known or can be prepared by known methods (compare quoted literature and European Pat. No. 123,095).

The reaction conditions, such as solvent, temperatures and ratios of amounts, for process H are the same as already indicated for processes A to G.

The starting compounds of the formula XI are new and are prepared by processes A to G as indicated under section 1).

Suitable bases are the customary bases such as, for example, alkali metal or alkaline earth metal hydroxides, in particular sodium, potassium and calcium hydroxide, or amines such as ammonia, triethylamine and pyridine. The cyclization can be carried out in the customary solvents, such as aromatic hydrocarbons (for example benzene and toluene), alcohols (ethanol, propanol and methanol) or acetic acid. The cyclization is carried out at temperatures from 10° C. to 200° C., preferably at 20° to 150° C.

The pyrolysis can be carried out with or without solvent. All customary inert organic solvents are suitable as the solvent where appropriate. These include, preferably, hydrocarbons such as benzene, toluene or xylene, tetralin, petroleum fractions, ethers, such as diethyl ether, dioxane, tetrahydrofuran, glycol monoethyl or diethyl ether, halogenated hydrocarbons such as dichloromethane, trichloromethane or tetrachloromethane, dichloroethylene or trichloroethylene.

The pyrolysis is carried out in a temperature range from 20° C. to 300° C., preferably from 40° to 250° C.

The pyrolysis can be carried out under atmospheric, elevated or reduced pressure. In general, it is carried out under atmospheric pressure. Process I is preferred.

The abovementioned preparation processes are merely indicated for illustration. The preparation of the compounds of the formula I is not restricted to these processes, but every modification of these processes can be used in a similar manner for the preparation of the compounds according to the invention.

The compounds according to the invention exist in stereoisomeric forms which are related either as image and mirror image (enantiomers) or are not related as image and mirror image (mixtures of diastereomers). The invention relates to both the antipodes and the racemic forms and mixtures of diastereomers. The racemic forms can, as can the diastereomers, be separated in a known manner into the stereoisomerically uniform constituents (compare E. L. Eliel, Stereochemistry of Carbon Compounds, McGraw Hill, 1962).

The compounds according to the invention have a positive inotropic and coronary-dilating action and thus exhibit a valuable pharmacological spectrum of actions which could not have been predicted. They can be used as agents affecting the circulation, as coronary therapeutic agents, antiarrhythmics, for the treatment of cardiac insufficiency and for influencing the level of blood sugar.

The action enhancing the contractility of the heart was found in the isolated atria of guineapig hearts.

For this purpose, the left atria of guineapig hearts are isolated and suspended in a thermostated organ bath which contains an isotonic mineral salt solution which is adjusted to suit the ionic medium and the pH of body fluids, and contains suitable nutrients. A gas mixture consisting of oxygen and carbon dioxide was passed through this organ bath, the content of carbon dioxide being calculated to keep the pH of the organ bath constant. The left atria were tensioned in the organ bath, and the tension was recorded by means of a force sensor, a particular basic tone being set up. The left atria were then subjected to continuous electrical stimulation at particular intervals, and the contractions taking place during this were recorded. Recording of the contractions was continued after administration of the active compound.

| Example No. | Increase in contractions at $10^{-5}$ g/ml [%] |
|---|---|
| 2 | +16.5 |
| 6 | +50 |
| 7 | +10 |
| 12 | +78 |
| 14 | +15 |
| 15 | +33 |

-continued

| Example No. | Increase in contractions at $10^{-5}$ g/ml [%] |
|---|---|
| 30 | +18 |
| 31 | +32 |
| 33 | +37 |

The coronary-dilating action was found in the isolated, perfused guineapig heart.

The hearts of Albino guineapigs weighing 250 to 350 g were used for this purpose. The animals are killed by a blow to the head, the thorax is opened, a metal cannula is tied into the exposed aorta, and the left atrium is opened. The heart, together with the lungs, was dissected out of the thorax and connected via the aorta cannula to the perfusion apparatus, with perfusion continuing. The lungs were removed at the roots of the lungs. The perfusion medium used was Krebs-Henseleit solution (2) (118.5 mmol/l NaCl, 4.75 mmol/l KCl, 1.19 mmol/l $KH_2PO_4$, 1.19 mmol/l $MgSO_4$, 25 mmol/l $NaHO_3$, 0.013 mmol/l NaEDTA), the $CaCl_2$ in which being varied as required, but as a rule being 1.2 mmol/l.

10 mmol/l glucose was added as an energy-providing substrate. The solution was filtered to remove particles before the perfusion. Carbogen (95% $O_2$, 5% $CO_2$) was passed through the solution to maintain the pH of 7.4. The hearts were perfused at a constant flow rate (10 ml/min) by means of a peristaltic pump at 32° C.

To measure the heart function, a liquid-filled latex balloon, which was connected via a liquid column to a pressure sensor, was introduced through the left atrium into the left ventricle. The perfusion pressure was recorded by means of a pressure sensor which was connected to the perfusion system upstream of the heart. Under these conditions, a reduction in the perfusion pressure indicated coronary dilatation.

The compounds according to the invention were infused in suitable dilutions into the perfusion system a short distance upstream of the isolated hearts.

| Example No. | Reduction in resistance at $10^{-6}$ g/ml [%] |
|---|---|
| 2 | −39 |
| 6 | −23 |
| 7 | −8 |
| 12 | −21 |
| 14 | −33 |
| 15 | −55 |
| 30 | −21 |
| 31 | −83 |
| 33 | −50 |

The new active compounds can be converted in a known manner into the customary formulations, such as tablets, capsules, coated tablets, pills, granules, aerosols, syrups, emulsions, suspensions and solutions, using inert, non-toxic, pharmaceutically suitable vehicles or solvents. The therapeutically active compounds should in each case be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example, when using water as a diluent, organic solvents can optionally be used as auxiliary solvents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid vehicles, such as, for example, natural rock powders (for example kaolins, aluminas, talc and chalk), synthetic rock powders (for example highly disperse silica and silicates) and sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatine and the like. Furthermore, lubricants such as magnesium stearate, sodium lauryl sulphate and talc can also be used when making tablets. In the case of aqueous suspensions and/or elixirs which are intended for oral use, the active compounds can be mixed with various flavor-improving agents or colorants in addition to the abovementioned auxiliaries.

In the case of parenteral administration, solutions of the active compounds, employing suitable liquid vehicles, can be used.

In general, it has proved advantageous, in the case of intravenous administration, to administer amounts of about 0.001 to 1 mg/kg, preferably about 0.01 to 0.5 mg/kg, body weight to achieve effective results, and in the case of oral administration, the dosage is about 0.01 to 20 mg/kg, preferably 0.1 to 10 mg/kg, body weight.

Nevertheless, it can at times be necessary to deviate from the amounts mentioned, and in particular to do so as a function of the body weight of the experimental animal or of the nature of the administration method, but also because of the species of animal and its individual behavior towards the medicament, or the nature of the formulation of the medicament and the time or interval over which the administration takes place. Thus it can suffice in some cases to manage with less than the abovementioned minimum amount, while in other cases the upper limit mentioned must be exceeded. Where relatively large amounts are administered, it can be advisable to divide these into several individual administrations over the course of the day. The same dosage range is envisaged for administration in human medicine. In this connection, the above statements similarly apply.

Preparation Examples

EXAMPLE 1

Ethyl 2-methyl-5-oxo-4-(2-phenylsulphonyloxy)phenyl-1,4,5,7-tetrahydrofuro [3,4-b]pyridine-3-carboxylate

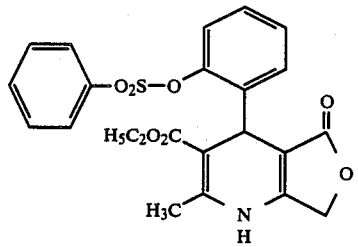

(a) 20 mmol each of 2-(2-phenylsulphonyloxy)benzaldehyde, ethyl β-aminocrotonate and ethyl γ-chloroacetoacetate are boiled under reflux in ethanol. The solution is then concentrated, and the residue is taken up in dichloromethane. The organic phase is washed with water, dried and evaporated. The residue is crystallized from methanol.

(b) 20 mmol each of 2-(phenylsulphonyloxy)benzaldehyde, ethyl β-aminocrotonate and ethyl γ-acetoxyacetoacetate are boiled in ethanol overnight, then KOH is added, and boiling is continued for 15 min.

The mixture is concentrated, water is added, and the mixture is extracted by shaking with dichloromethane. The organic phase is dried and concentrated. The residue is crystallized from methanol.

Melting point: 96°–100° C.

EXAMPLE 2

Methyl 1,4-dihydro-2,6-dimethyl-5-nitro-4-(2-p-tolylsulphonyloxy)phenylpyridine-3-carboxylate

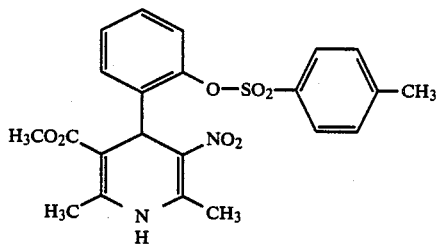

20 mmol each of nitroacetone, methyl β-aminocrotonate and 2-(p-tolylsulphonyloxy)benzaldehyde are boiled in 50 ml of ethanol for 3 h, the solution is concentrated, and the residue is chromatographed on silica gel using toluene/ethyl acetate.

Melting point: 184°–187° C.

EXAMPLE 3

40 mmol each of 2-(4-nitrobenzoyloxy)benzaldehyde, nitroacetone and methyl β-aminocrotonate are heated to reflux in 60 ml of ethanol for 2 h. Crystallization takes place on cooling the reaction mixture. The solid is filtered off with suction and washed with ethanol. 3.9 g (21.5%) of yellow crystals are obtained.

Melting point: 245° C.

The examples listed in the following tables are obtained in analogy to the processes described above:

TABLE 1

| Example No. | $R^1$ | $R^3$ | $R^6$ | Melting point [°C.] |
|---|---|---|---|---|
| 4 | $CH_2CH_3$ | H | phenyl-CH₃ | 121–3 |
| 5 | $CH_3$ | H | phenyl-CH₃ | 175–8 |
| 6 | $CH_2CH_3$ | H | $(CH_2)_4Cl$ | amorph. |
| 7 | $CH_2CH_3$ | H | 3,5-diisopropylphenyl | 218–20 |
| 8 | $CH_2CH_3$ | H | 2,4,5-trichlorophenyl | 245–7 |
| 9 | $CH_3$ | H | phenyl | 201–5 |
| 10 | $CH_3$ | $CH_3$ | phenyl | 165–9 |
| 11 | $(CH_2)_3CH_3$ | H | phenyl | 88–91 |

TABLE 2
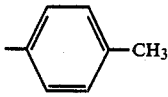
| Example No. | R¹ | R⁶ | R⁷ | Melting point [°C.] |
|---|---|---|---|---|
| 12 | CH$_2$CH$_3$ | 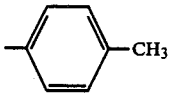 4-CH$_3$-C$_6$H$_4$ | H | 53-4 |
| 13 | (CH$_2$)$_2$OCH$_3$ | 4-CH$_3$-C$_6$H$_4$ | H | 210-2 |
| 14 | (CH$_2$)$_3$CH$_3$ | 4-CH$_3$-C$_6$H$_4$ | H | 176-8 |
| 15 | CH$_2$—CH=CH$_2$ | 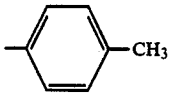 2-CH$_3$-C$_6$H$_4$ | H | amorph. |
| 16 | (CH$_2$)$_7$CH$_3$ | 2-CH$_3$-C$_6$H$_4$ | H | oil |
| 17 | CH$_3$ | 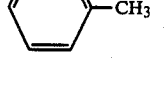 C$_6$H$_5$ | H | 220-5 |
| 18 | CH$_2$CH$_3$ | C$_6$H$_5$ | H | 127-9 |
| 19 | CH$_3$ | 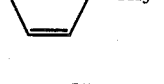 3-Cl-C$_6$H$_4$ | H | 70-4 |
| 20 | CH$_2$CH$_3$ | 3-Cl-C$_6$H$_4$ | H | amorph. |
| 21 | CH$_2$CH$_3$ | 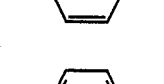 4-Cl-C$_6$H$_4$ | H | 121-5 |

TABLE 2-continued
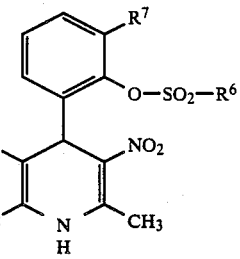
| Example No. | R¹ | R⁶ | R⁷ | Melting point [°C.] |
|---|---|---|---|---|
| 22 | $CH_3$ | 3-nitrophenyl | H | 96–9 |
| 23 | $CH_2CH_3$ | 3-nitrophenyl | H | 72–80 |
| 24 | $CH_3$ | 4-methylphenyl | $OCH_3$ | 190–210 |
| 25 | $CH_2CH_3$ | 4-methylphenyl | $OCH_3$ | 169–87 |
| 26 | $CH_3$ | 2-methylphenyl | H | 210–6 |
| 27 | $CH_2CH_3$ | 2-methylphenyl | H | 278–85 |
| 28 | $CH_3$ | $(CH_2)_{15}CH_3$ | H | 126 |
| 29 | $CH_2CH_3$ | $(CH_2)_{15}CH_3$ | H | Oil |
| 30 | $CH_3$ | 4-chlorophenyl | H | 210–6 |
| 31 | $CH_3$ | 4-chloro-3-nitrophenyl | H | amorph. |
| 32 | $CH_2CH_3$ | 4-chloro-3-nitrophenyl | H | amorph. |

TABLE 2-continued

Structure:

R¹O₂C— and —NO₂ substituents on a 1,4-dihydropyridine ring with 2,6-dimethyl and NH; the 4-position bears a phenyl ring with ortho O—SO₂—R⁶ and R⁷ substituent.

| Example No. | R¹ | R⁶ | R⁷ | Melting point [°C.] |
|---|---|---|---|---|
| 33 | CH₂CH₃ | —CH₂—(bicyclic ketone, camphor-like) | H | amorph. |
| 34 | CH₂CH₃ | 2,4,6-triisopropylphenyl | H | 107–9 |
| 35 | CH₂CH₃ | 2,4,5-trichlorophenyl | H | 94–7 |
| 36 | CH₃ | 2,4,6-triisopropylphenyl | H | 114 |
| 37 | CH₃ | 2,4,5-trichlorophenyl | H | 120 |
| 38 | CH₂CH₃ | 2-naphthyl | H | 170–2 |
| 39 | CH₂CH₃ | 2,5-dichlorophenyl | H | 108–11 |

TABLE 2-continued

[Structure: dihydropyridine with R¹O₂C, NO₂, two CH₃ groups, NH; phenyl substituent bearing O-SO₂-R⁶ and R⁷]

| Example No. | R¹ | R⁶ | R⁷ | Melting point [°C.] |
|---|---|---|---|---|
| 40 | CH₃ | 2-naphthyl | H | 156–60 |
| 41 | CH₃ | 2,5-dichlorophenyl | H | 135–40 |
| 42 | CH₂—phenyl | 4-methylphenyl | H | amorph. |
| 43 | CH₂—cyclohexyl | 4-methylphenyl | H | amorph. |
| 44 | CH₂CH₃ | 2-thienyl | H | foam |
| 45 | CH₂CH₃ | 4-(NCOCH₃)phenyl | H | 233 |
| 46 | CH₃ | 4-(SCF₃)phenyl | H | foam |
| 47 | CH₃ | 5-chloro-2-thienyl | H | foam |

TABLE 3

[Structure: dihydropyridine with 2-O-C(=O)-R6 phenyl at 4-position, R1O2C at 3, NO2 at 5, R2 at 2, CH3 at 6, NH]

| Example No. | R¹ | R² | R⁶ | Melting point [°C.] |
|---|---|---|---|---|
| 48 | CH₂CH₃ | CH₃ | –C₆H₅ | 180–1 |
| 49 | CH₃ | CH₃ | –C₆H₅ | 190–3 |
| 50 | CH₃ | CH₂CH₃ | –C₆H₅ | 198–200 |
| 51 | C₄H₉ | CH₃ | –C₆H₅ | 175–8 |
| 52 | CH₂CH₃ | CH₃ | –C₆H₄-OCH₃ (p) | 146 |
| 53 | CH₃ | CH₃ | –CH₂–C₆H₅ | 140 |
| 54 | CH₃ | CH₂CH₃ | –C₆H₄-NO₂ (p) | 237 |
| 55 | CH₃ | CH₃ | –CH=CH–C₆H₅ | 222 |

TABLE 4

[Structure: dihydropyridine with 2-O-C(=O)-NH-R6 phenyl at 4-position, R1O2C at 3, NO2 at 5, H3C at 2, CH3 at 6, NH]

| Example No. | R¹ | R⁶ | Melting point [°C.] |
|---|---|---|---|
| 56 | CH₃ | C₆H₅ | 144–50 |
| 57 | CH₂CH₃ | C₆H₅ | 227–33 |

EXAMPLE 58

Ethyl 1,4-dihydro-2,6-dimethyl-4-(2-benzoyloxy-3-methoxyphenyl)-5-nitropyridine-3-carboxylate of melting point: 195° C.

EXAMPLE 59

Ethyl 1,4-dihydro-2,6-dimethyl-4-(2-benzenesulphonyloxyphenyl)-5-nitropyridine-3-carboxylate of melting point: 222° C.

It will be understood that the specification and examples are illustrative but not limitative of the present invention and that other embodiments within the spirit and scope of the invention will suggest themselves to those skilled in the art.

We claim:

1. A dihydropyridine exhibiting a positive inotropic effect of the formula

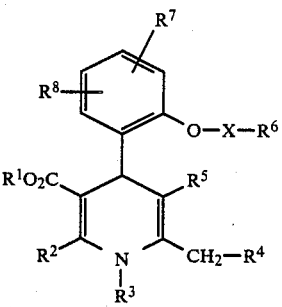

in which

R¹ represents straight-chain, branched or cyclic alkyl or alkenyl each of which has up to 8 C atoms and is optionally interrupted in the chain by one oxygen or sulphur atom and is optionally substituted by phenyl, cyano, one or more fluorine atoms or N-benzyl-N-methylamino, R² represents methyl, hydroxymethyl or ethyl, or represents cyano, R³ represents hydrogen, or represents methyl or ethyl, R⁴ represents hydrogen or hydroxyl, represents methyl or ethyl, represents chlorine or bromine, or represents —OOC—CH₃, R⁵ represents nitro, or represents CO₂R⁹, wherein R⁹ and R⁴ together denote a direct bond, X represents >C=O, —SO₂— or —CO—NH—, R⁶ represents straight-chain, branched or cyclic alkyl or alkenyl each of which has up to 16 C atoms and is optionally substituted by phenyl or one or more fluorine or chlorine atoms, represents thienyl, furyl or pyridyl which is optionally substituted by chlorine or methyl, or represents phenyl or naphthyl each of which optionally carries up to 3 identical or different substituents from the group consisting of fluorine, chlorine, nitro, C₁-C₄-alkyl, methoxy, methylthio, trifluoromethoxy, trifluoromethylthio, trifluoromethyl or acetylamino, or represents the radical

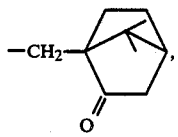

and

R⁷ and R⁸ are identical or different and represent hydrogen, represent C₁-C₄-alkoxy, represent chlorine, represent C₁-C₄-alkyl, represent nitro, or represent trifluoromethyl.

2. A compound according to claim 1, wherein such compound is methyl 1,4-dihydro-2,6-dimethyl-5-nitro-4-(2-p-tolylsulphonyloxy)phenylpyridine-3-carboxylate of the formula

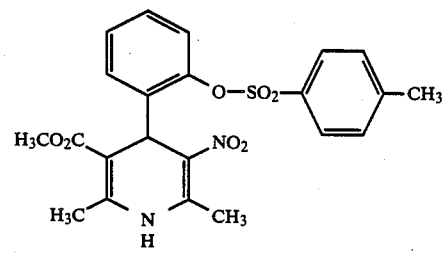

or a pharmaceutically acceptable salt thereof.

3. A compound according to claim 1, wherein such compound is methyl 1,2-dimethyl-5-oxo-4-(2-phenylsulphonyloxy)phenyl-1,4,5,7-tetrahydrofuro[3,4-b]pyridine-3-carboxylate of the formula

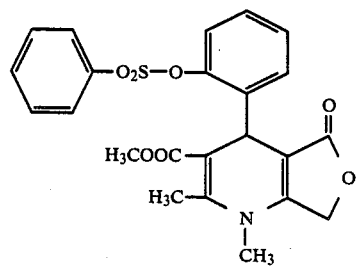

or a pharmaceutically acceptable salt thereof.

4. A compound according to claim 1, wherein such compound is ethyl 4-(2-benzoyloxy-phenyl)-1,4-dihydro-2,6-dimethyl-5-nitro-pyridine-3-carboxylate of the formula

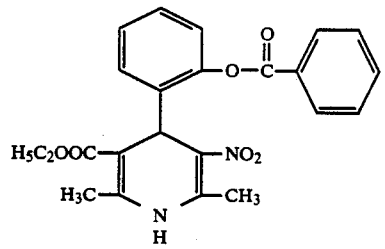

or a pharmaceutically acceptable salt thereof.

5. A compound according to claim 1, in which

R¹ represents straight-chain, branched or cyclic alkyl or alkenyl each of which has up to 8 C atoms and is optionally interrupted in the chain by one oxygen atom and is optionally substituted by phenyl or fluorine, R² represents methyl, hydroxymethyl or cyano, R⁴ represents hydrogen, hydroxyl, chlorine, bromine, or —OOC—CH₃, R⁶ represents straight-chain, branched or cyclic alkyl or alkenyl each of which has up to 12 C atoms and is optioally substituted by phenyl or one or more fluorine or chlorine atoms, represents thienyl or pyridyl which is optionally substituted by chlorine or methyl, or represents phenyl or naphthyl each of which optionally carries up to 3 identical or different substituents from the group consisting of fluorine, chlorine, nitro, C₁-C₄-alkyl, methoxy, methylthio, trifluoromethoxy, trifluoromethylthio, trifluoromethyl or acetylamino, or represents the radical

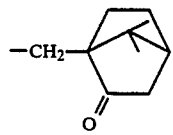

6. A circulation active composition comprising a positive inotropic effective amount of a compound or salt according to claim 1 and a diluent.

7. A unit dose of a composition according to claim 6 in the form of a tablet, capsule or ampule.

8. A method of improving the circulation of a patient in need thereof which comprises administering to said patient a positive inotropic effective amount of a compound or salt according to claim 1.

9. The method according to claim 8, wherein such compound is methyl 1,4-dihydro-2,6-dimethyl-5-nitro-4-(2-p-tolylsulphonyloxy)phenylpyridine-3-carboxylate, methyl 1,2-dimethyl-5-oxo-4-(2-phenylsulphonyloxy)phenyl-1,4,5,7-tetrahydrofuro[3,4-b]pyridine-3-carboxylate or ethyl 4-(2-benzoyloxy-phenyl)-1,4-dihydro-2,6-dimethyl-5-nitro-pyridine-3-carboxylate, or a pharmaceutically acceptable salt thereof.

* * * * *

UNITED STATES PATENT AND TRADEMARK OFFICE
CERTIFICATE OF CORRECTION

PATENT NO. : 4,772,612

DATED : September 20, 1988

INVENTOR(S) : Siegfried Goldmann, et al

It is certified that error appears in the above-identified patent and that said Letters Patent is hereby corrected as shown below:

| | |
|---|---|
| Col. 2, line 14 | Delete "$C_1$-$C_8$alkyl" and substitute --$C_1$-$C_8$-alkyl-- |
| Col. 2, line 20 | Before "-$C_4$-alkyl" delete "∫" |
| Col. 2, line 44 | Correct --being-- |
| Col. 4, line 6 | After "can be" delete "n" and substitute --in-- |
| Col. 4, line 45 | Delete "compound" and substitute --compounds-- |
| Col. 9, line 51 | Delete "15°C" and substitute --150°C-- |
| Col. 12, line 13 | Delete "40° to" and substitute --40°C to-- |
| Col. 13, line 23 | Delete "$NaHO_3$" and substitute --$NaHCO_3$-- |
| Col. 28, line 30 | Correct --optionally-- |

Signed and Sealed this

Nineteenth Day of September, 1989

Attest:

DONALD J. QUIGG

Attesting Officer

Commissioner of Patents and Trademarks